(12) United States Patent
Mosler et al.

(10) Patent No.: US 6,669,737 B2
(45) Date of Patent: Dec. 30, 2003

(54) FOOT INSERT FOR AN ARTIFICIAL FOOT

(75) Inventors: Luder Mosler, Duderstadt (DE); Martin Pusch, Duderstadt (DE)

(73) Assignee: Otto Bock HealthCare GmbH, Duderstadt (DE)

( * ) Notice: Subject to any disclaimer, the term of this patent is extended or adjusted under 35 U.S.C. 154(b) by 0 days.

(21) Appl. No.: 10/148,928

(22) PCT Filed: Aug. 8, 2001

(86) PCT No.: PCT/DE01/03035

§ 371 (c)(1),
(2), (4) Date: Sep. 13, 2002

(87) PCT Pub. No.: WO02/30340

PCT Pub. Date: Apr. 18, 2002

(65) Prior Publication Data

US 2003/0045944 A1 Mar. 6, 2003

(30) Foreign Application Priority Data

Oct. 7, 2000 (DE) .......................... 100 49 714

(51) Int. Cl.⁷ .................................. A61F 2/66
(52) U.S. Cl. .......................... 623/55; 623/52
(58) Field of Search ............ 623/47, 49, 50, 623/52, 53, 54, 55, 48, 51, 56

(56) References Cited

U.S. PATENT DOCUMENTS 4,959,073 A   9/1990   Merlette ................. 623/55
5,549,711 A   8/1996   Bryant .................... 623/52
5,800,570 A   9/1998   Collier ................... 623/55

FOREIGN PATENT DOCUMENTS

| DE | 4037928 A1 | 11/1990 |
|---|---|---|
| DE | 29820904 U1 | 11/1998 |
| DE | 19962851 A1 | 12/1999 |
| EP | 0884033 A2 | 11/1998 |
| WO | WO 00/71061 | * 11/2000 |
| WO | WO 01/47444 A1 | 11/2000 |

* cited by examiner

Primary Examiner—Corrine McDermott
Assistant Examiner—Thomas J Sweet
(74) Attorney, Agent, or Firm—Whitham, Curtis & Christofferson, P.C.

(57) ABSTRACT

The invention relates to a resilient foot insert for an artificial foot. According to the invention, this foot insert consists of at least two springs (1, 2) which are connected to one another and which together-in side view, in the unloaded state, enclose an approximately triangular spring deflection space (3), the upper, approximately roof-shaped spring (1) having, in the roof top area, an adapter attachment (4) and, starting from the latter, a heel branch (hereinafter "heel spring 6") which extends downward in a concave curve into the heel area (5), and a forefoot branch (hereinafter "forefoot spring 8") which extends downward in a concave curve into the forefoot area (7), the free branch ends (6a, 8a) being connected to a separate base spring (2) which delimits the bottom of the spring deflection space (3).

22 Claims, 5 Drawing Sheets

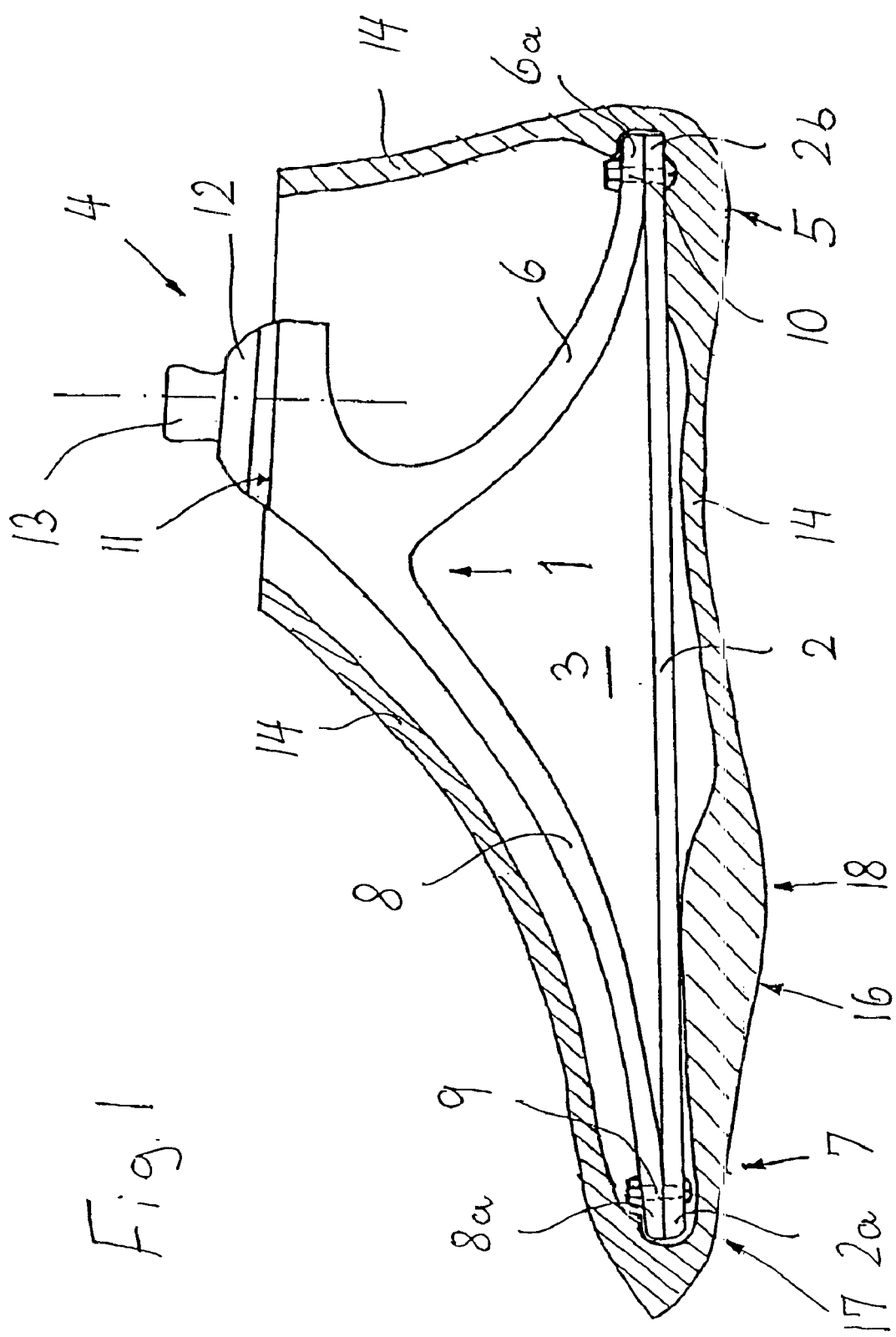

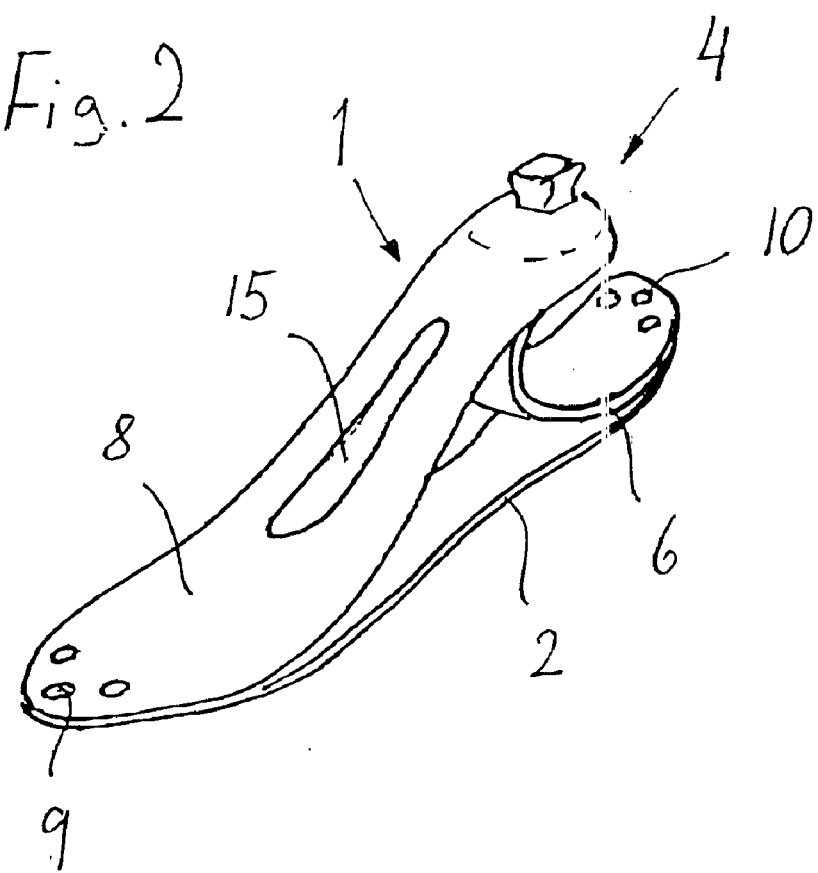
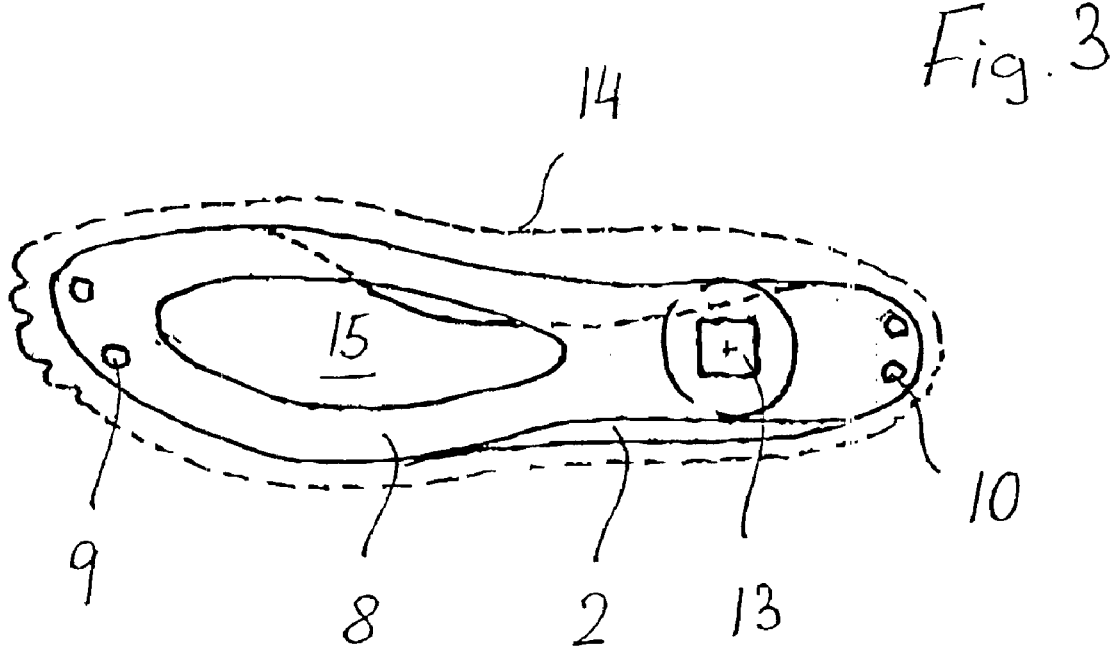

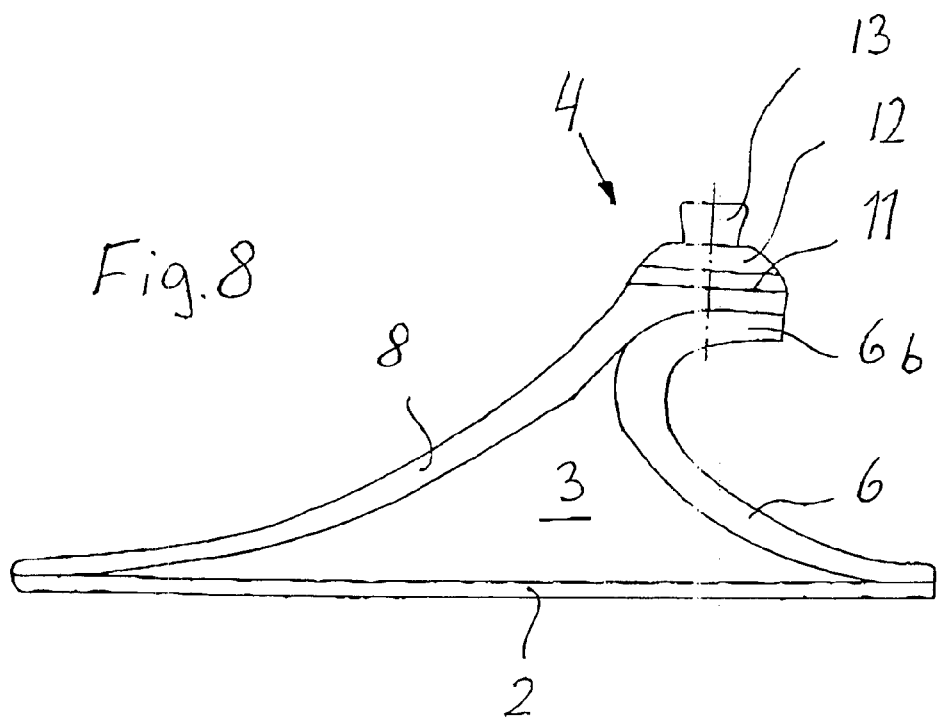
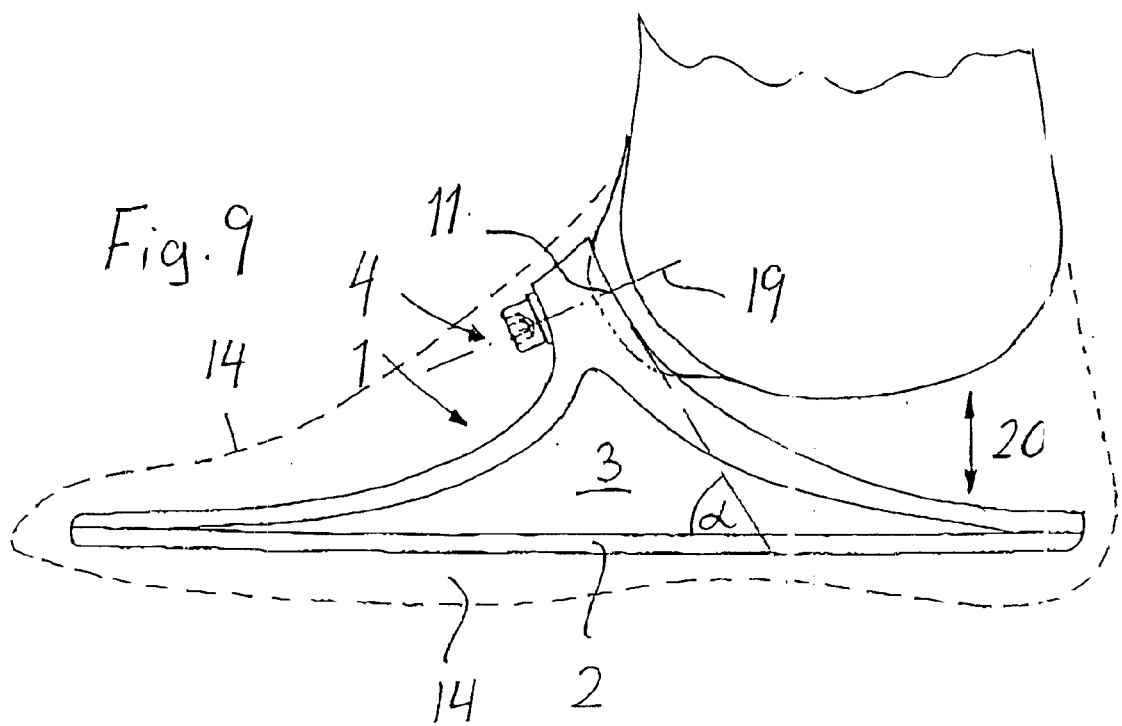

FOOT INSERT FOR AN ARTIFICIAL FOOT

The invention relates to a resilient foot insert for an artificial foot.

A jointless prosthetic foot with a resilient foot insert which takes up and transmits the prosthesis loads is disclosed, for example, in DE 40 37 928 A1 and EP 0 648 479 A1. Elastic foot inserts are also to be found in U.S. Pat. Nos. 4,959,073, 5,549,711 and 5,800,570, and in EP 0 884 033 A2 and DE 298 20 904 U1.

The object of the invention is to develop a resilient foot insert for a prosthetic foot which has a progressive ankle moment profile, stores energy and permits an elastic ML (medial-lateral) mobility.

According to the invention, this object is achieved by a resilient foot insert for an artificial foot, consisting of at least two springs which are connected to one another and which together in side view, in the unloaded state, enclose an approximately triangular spring deflection space, the upper, approximately roof-shaped spring having, in the roof top area, an adapter attachment an, starting from the latter, a heel branch (hereinafter "heel spring") which extends downward in a concave curve into the heel area, and a forefoot branch (hereinafter "forefoot spring") which extends downward in a concave curve in the forefoot area, the free branch ends being connected to a separate, flexurally rigid base spring which delimits the bottom of the spring deflection space and which interacts with a rolling contour in such a way that, at the start of the loading of the forefoot during the rolling action (i.e., walking in a heel-to-toe fashion), the force is first introduced in the are of the ball of the foot, with forefoot spring and base spring being configured in terms of shape and flexural elasticity in such a way that, under the effect of an increasing load in the forefoot area, the forefoot spring and base spring successively bear against one another in this are by respective bending.

Thus, according to the invention, this foot insert is characterized by the forefoot spring and base spring being configured in terms of shape and elasticity in such a way that, with increasing load in the forefoot area, the forefoot spring and base spring come to successively bear against one another in this area. By means of this successive bearing on the base spring, the forefoot spring effects a progressive ankle moment profile. At the start of loading of the forefoot, the force is first introduced in the area of the ball of the foot, by which means the base spring is mounted between heel spring and forefoot spring and experiences three-point bending. There is then a serial connection of the flexural strengths of forefoot spring and base spring (on this point see also the view in FIG. 6). In the further course of the step, the foot effects a rolling action and increasingly loads the forefoot spring directly. The base spring additionally supports the moments in the forefoot spring and is now bent in the opposite direction. There is a parallel connection of the flexural strengths (on this point see also the view in FIG. 7). The course of the loading of the forefoot is thus marked by an increasing stiffening or progression of the spring behavior.

The contact points of the prosthetic foot with the ground or shoe determine the site of introduction of force. This has an influence on the biomechanics of the foot, but also controls the loading of the mechanical structures of the foot. Since the foot experiences an angle movement during the stance phase, the point of introduction of force can be controlled by a suitable rolling geometry. It does not matter whether this geometry is integrated into the configuration of the base spring (see FIG. 4 for example), applied to the base spring (see FIG. 5) or is a feature of the surrounding cosmetic covering (see FIG. 1). In all these cases, the base spring interacts on the underside with a rolling contour which slopes downward from the toe area to the ball area, then slopes upward again, and is shaped as a downward bulge formation in the heel area.

To achieve the effect which is sought, it is also expedient if the front free branch end of the forefoot spring is connected to the front end of the base spring, and if the rear free branch end of the heel spring is connected to the rear end of the base spring.

The characteristics of the foot can be deliberately modified by using base springs of different degrees of rigidity. For this purpose, the connections between the base spring and the two branch ends of the upper spring are made releasable.

ML movement can be generated by reducing the torsional rigidity of the forefoot spring. This can be realized by means of the forefoot spring having an oblong recess extending in its longitudinal direction, or by the forefoot spring being split into two part-springs in its longitudinal direction. In this way it is also possible to set different progression characteristics for the inside face and outside face of the foot. The instantaneous center of the ML rotation lies in the physiologically desirable manner above the ground plane, whereas rotation about the longitudinal axis of the leg is hardly possible.

At least one of the springs is preferably made of a polymer material, which is expediently a fiber composite. With a fiber composite, the introduction of force into the springs can be enhanced if the springs are designed individually, especially if parts of the adapter are a component part of one of the springs. For this reason, it is therefore expedient if forefoot spring and heel spring form separate structural parts which are connected to one another in the area of the adapter attachment. It is of further advantage here if at least the spherical cap of the adapter attachment is an integral component part of the forefoot spring. A construction which is particularly favorable in respect of transmission of force is obtained if the forefoot spring, in the area of its adapter attachment, is supported on the upper branch end of the heel spring.

If the resilient foot insert is to be used in cases where the amputation levels are very low, particularly in cases of disarticulation of the ankle joint (on this point, see also the view in FIG. 9), it is expedient if the adapter attachment is positioned anteriorly of the ankle area of a natural foot and has an attachment surface enclosing an acute angle with the base spring. In this way, the space under the prosthesis shaft can be used as a spring deflection space for the heel branch. In the case of this attachment, the moments on the adapter between loading of the heel and loading of the forefoot are more balanced and lower than in the case of an attachment in the ankle area. The necessary structural strength is thus easier to achieve.

A number of embodiments of the invention serving as examples are shown schematically in the drawing, where:

FIG. 1 shows, in a longitudinal section, an artificial foot consisting of a resilient foot insert which is surrounded by a cosmetic covering;

FIG. 2 shows a resilient foot insert in a perspective view;

FIG. 3 shows a resilient foot insert in a plan view;

FIG. 8 shows a resilient foot insert with separately formed forefoot spring and heel spring, and FIG. 9 shows a resilient foot insert for use with low amputation levels.

Figure 4:
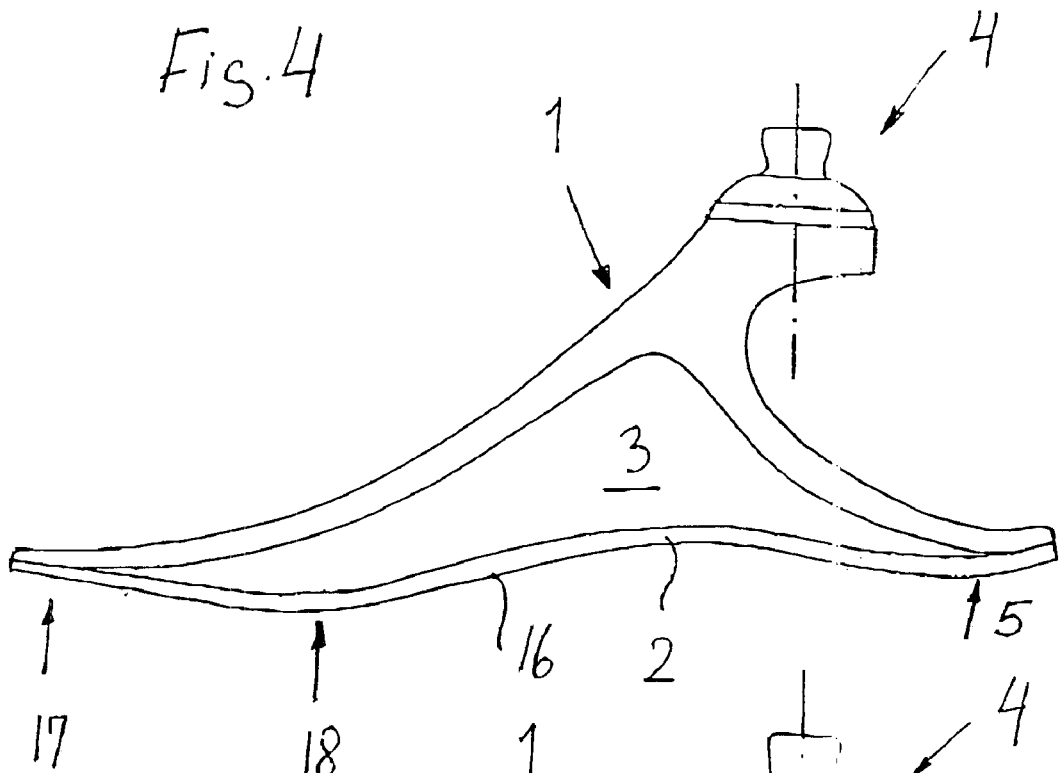
FIG. 4 shows a side view of a resilient foot insert with a base spring bent in the shape of a rolling contour.
Figure 5:
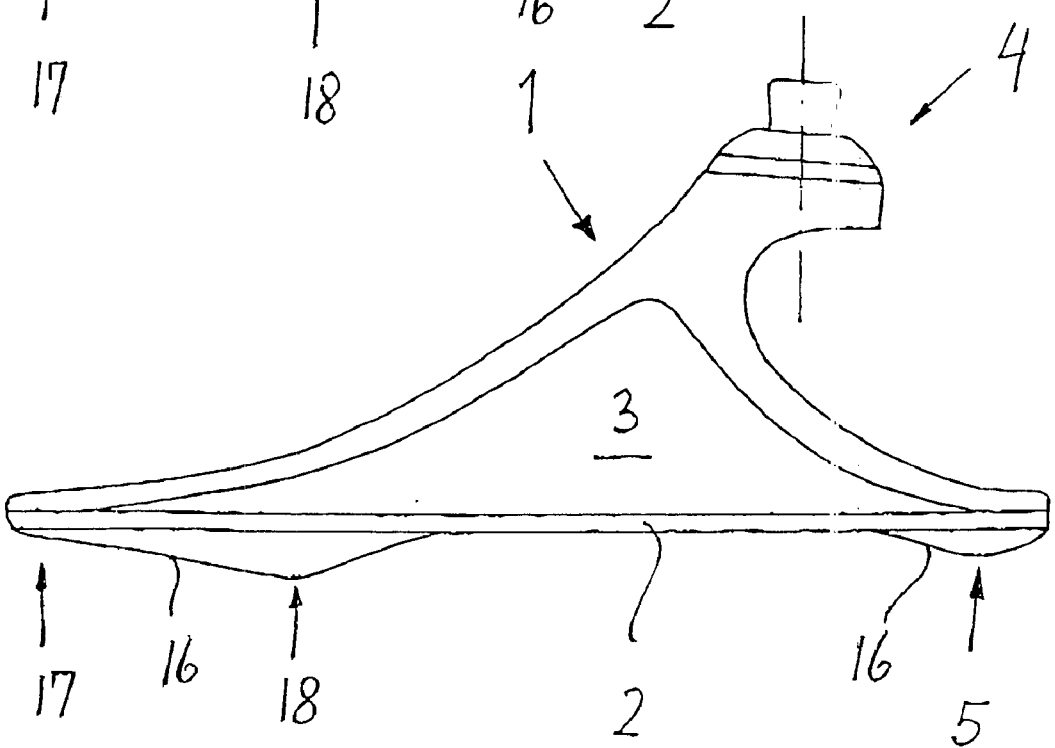
FIG. 5 shows, in a view according to FIG. 4, an elastic foot insert with a straight base spring with applied rolling contour.
Figure 6:
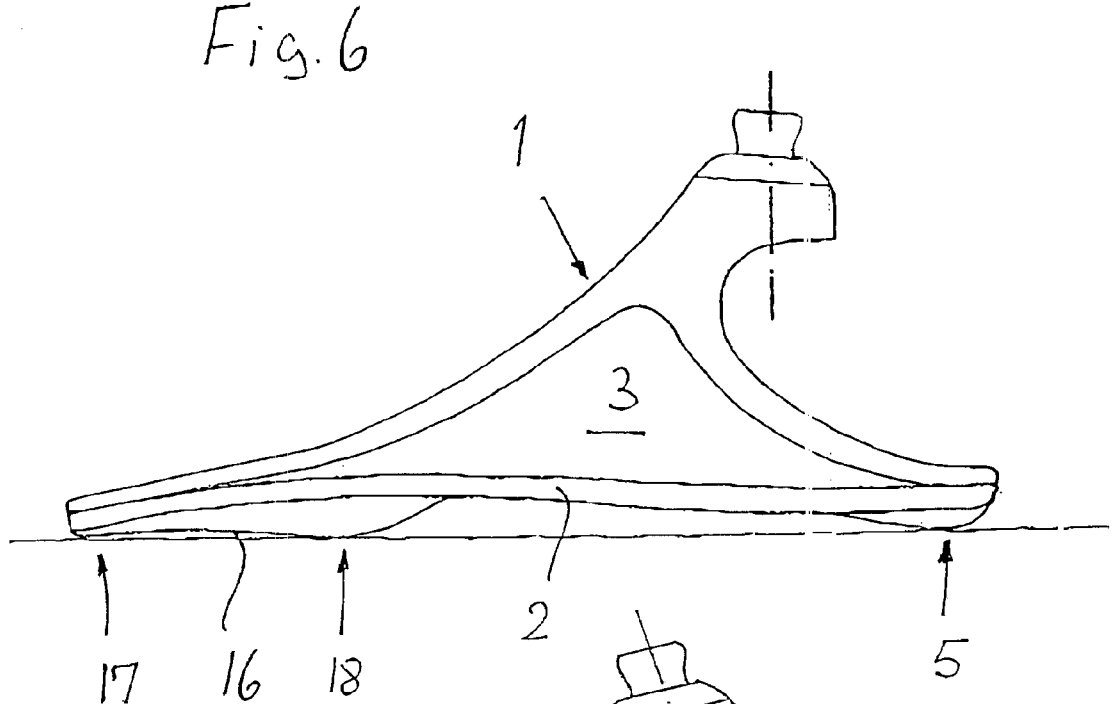
FIG. 6 shows the elastic foot insert according to FIG. 5 at the start of loading of its forefoot.
Figure 7:
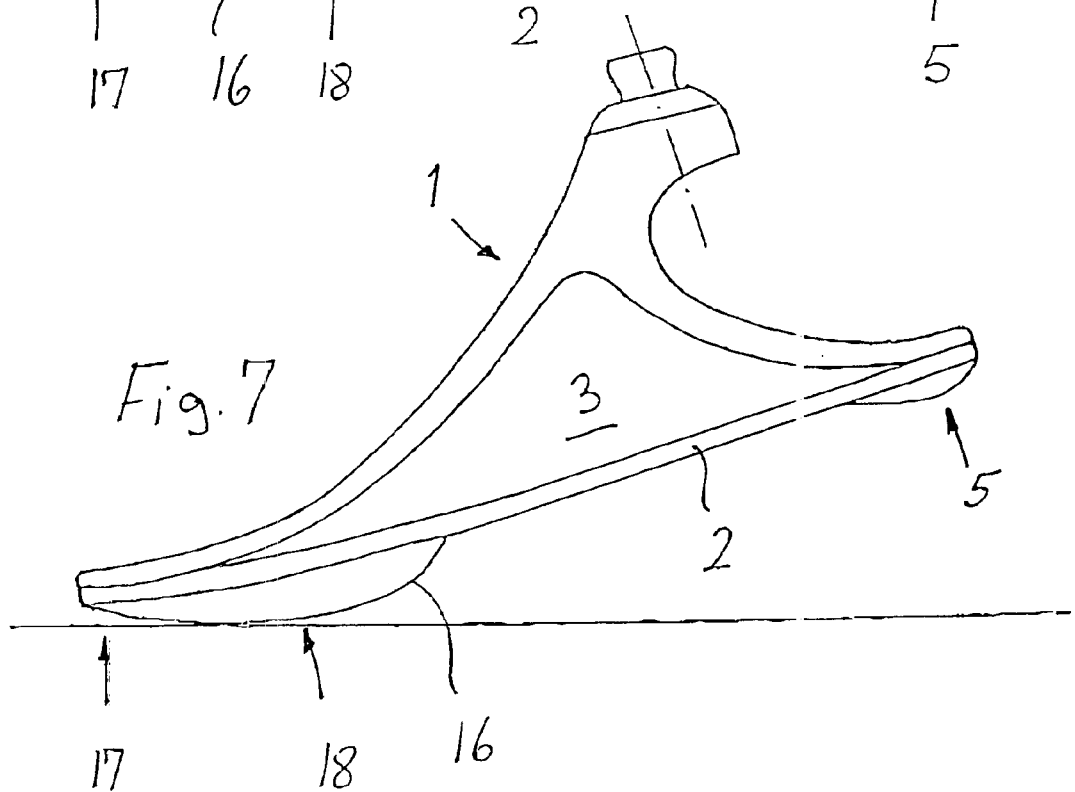
FIG. 7 shows the elastic foot insert according to FIG. 5 with the forefoot spring directly loaded.

FIG. 1 shows a resilient foot insert for an artificial foot. The foot insert here consists of an upper, approximately roof-shaped spring 1 which, together with a lower base spring 2, encloses an approximately triangular spring deflection space 3. In its roof area, the upper spring 1 has an adapter attachment 4 from which a heel spring 6 extends rearward and downward in a concave curve into the heel area 5, and a forefoot spring 8 extends forward and downward in a concave curve into the forefoot area 7. The front free branch end 8a of the forefoot spring 8 is connected to the front end 2a of the base spring 2, while the rear free branch end 6a of the heel spring 6 is connected to the rear end 2b of the base spring 2. The connections between the upper spring 1 and the base spring 2 can be designed as releasable connections 9, 10, as can be seen from FIG. 1. The base spring 2 is then exchangeable.

In the embodiments shown in FIGS. 1–8, the adapter attachment 4 in each case lies approximately in the ankle area of a natural foot and has an attachment surface 11 lying approximately parallel to the base spring 2. The adapter attachment 4 comprises a spherical cap 12 and a truncated pyramid 13 which lies with its point on the spherical cap 12.

It will also be seen from FIG. 1 that the resilient foot insert is surrounded by a cosmetic covering 14.

According to FIGS. 2 and 3, the forefoot spring 8 has an oblong recess 15 extending in its longitudinal direction.

According to FIG. 1, the substantially straight base spring 2 interacts with a rolling contour 16 which is formed by the underside of the cosmetic covering 14 and which slopes downward from the toe area 17 of the artificial foot to the ball area 18 and then slopes upward again and is shaped as a downward bulge formation in the heel area 5.

In the embodiment according to FIG. 4, the base spring 2 is bent directly in the shape of the rolling contour 16. In the modified embodiment according to FIG. 5, the rolling contour 16 is applied to the underside of the base spring 2 extending approximately in a straight line in the longitudinal direction.

In the embodiments shown in FIGS. 1–7 and 9, the upper spring 1 of the foot insert is made in one piece; the adapter attachment 4 forms an integral component part of this one-piece upper spring 1.

In the modified embodiment according to FIG. 8, the heel spring 6 and forefoot spring 8 form separate structural parts, which are connected to one another in the area of the adapter attachment 4. Here, the adapter attachment 4 forms an integral component part of the separate forefoot spring 8 which, in the area of the adapter attachment 4, is supported on the upper, rearwardly curved branch end 6b of the heel spring 6, which is approximately C-shaped.

FIG. 9 shows a resilient foot insert which is intended for use with very low amputation levels, in particular in cases of disarticulation of the ankle joint of the prosthesis user. Compared to the embodiment according to FIGS. 1 to 8, the adapter attachment 4 is here positioned anteriorly of the ankle area of a natural foot and has an attachment surface 11 enclosing an acute angle a with the base spring 2. Here too, the adapter attachment comprises a spherical cap 12 which permits limited angular adjustments of the shaft 19 indicated by a dot-and-dash line. This design results in a long heel travel 20.

What is claimed is:

1. A resilient foot insert for an artificial foot, comprising:
    at least two springs which are connected to one another and which together in side view, in an unloaded state, enclose an approximately triangular spring deflection space,
    an upper spring of said at least two springs is approximately roof-shaped defines a roof top area,
    an adapter attachment positioned in the roof top area,
    a heel spring which extends downward in a concave curve into a heel area,
    a forefoot spring which extends downward in a concave curve into a forefoot area,
    one bare spring extension of said heel spring and one bare spring extension of said forefoot spring being fixedly connected to a separate, flexurally rigid base spring which delimits a bottom of the spring deflections space and which interacts with a rolling contour in such a way that, at the start of loading of the forefoot area during walking in a heel-to-toe fashion, a force is first introduced in an area of a ball of a foot, with the forefoot spring and the base spring configured in terms of shape and flexural elasticity in such a way that said base spring is bent contrary to the concave curve of the forefoot spring and, under an effect of an increasing load in the forefoot area, the forefoot spring and base spring successively bear against one another in said forefoot area by the base spring now being bent in the opposite direction to its previous bending.

2. The foot insert as claimed in claim 1, wherein a front free branch end of the forefoot spring is connected to a front end of the base spring.

3. The foot insert as claimed in claim 1, wherein a rear free branch end of the heal spring is connected to a rear end of the base spring.

4. The foot insert as claimed in claim 1, further comprising releasable connections between the base spring and the two branch ends of the upper spring.

5. The foot insert as claimed in claim 1 wherein the forefoot spring has an oblong recess extending in a longitudinal direction.

6. The foot insert as claimed in claim 1 wherein the forefoot spring is split into two part-springs in a longitudinal direction.

7. The foot insert as claimed in claim 1 wherein the adapter attachment is positionable approximately in an ankle area of a natural foot and has an attachment surface lying approximately parallel to the base spring.

8. The foot insert as claimed in claim 1 wherein the adapter attachment is positionable anteriorly of an ankle area of a natural foot and has an attachment surface enclosing an acute angle ($\alpha$) with the base spring.

9. The foot insert as claimed in claim 1 wherein the adapter attachment is an integral component part of the upper spring.

10. The foot insert as claimed in claim 9, wherein the adapter attachment comprises a spherical cap.

11. The foot insert as claimed in claim 10, wherein the adapter attachment comprises a truncated pyramid.

12. The foot insert as claimed in claim 1 wherein the forefoot spring and heel spring form separate structural parts which are connected to one another in an area of the adapter attachment.

13. The foot insert as claimed in claim 10 wherein at least the spherical cap of the adapter attachment is an integral component part of the forefoot spring.

14. The foot insert as claimed in claim 13, wherein the forefoot spring, in an area of the adapter attachment, is supported on an upper branch end of the heal spring.

15. The foot insert as claimed in claim 1 wherein at least one of the forefoot, heel and base springs is made of a polymer material.

16. The foot insert as claimed in claim 15, wherein the polymer material is a fiber composite.

17. The foot insert as claimed in claim 1 wherein the base spring cooperates on an underside with a rolling contour which slopes downward from a toe area to the ball area and then slopes upward again.

18. The foot insert as claimed in claim 17, wherein the rolling contour is shaped as a downward bulge formation in a heel area.

19. The foot insert as claimed in claim 17 wherein the base spring is bent in the shape of the rolling contour.

20. The foot insert as claimed in claim 17 wherein the rolling contour is applied to an underside of the base spring extending approximately in a straight line in a longitudinal direction.

21. The foot insert as claimed in claim 17 the rolling contour is formed by an underside of a cosmetic covering which surrounds the foot insert.

22. The foot insert as claimed in claim 1 wherein the heel spring has a shape that, from a heel touching ground to a middle of a stance phase, an instantaneous center of rotation lies in an area of a natural ankle joint.

* * * * *